US007678153B2

(12) United States Patent
Katz et al.

(10) Patent No.: US 7,678,153 B2
(45) Date of Patent: Mar. 16, 2010

(54) SUBTALAR IMPLANT

(75) Inventors: Gary E. Katz, Gulfport, FL (US); David V. Mrak, North Street, MI (US); Steven E. Thueme, Columbus, MI (US)

(73) Assignee: Biopro, Inc., Port Huron, MI (US)

( * ) Notice: Subject to any disclaimer, the term of this patent is extended or adjusted under 35 U.S.C. 154(b) by 543 days.

(21) Appl. No.: 10/838,679

(22) Filed: May 4, 2004

(65) Prior Publication Data

US 2005/0251264 A1    Nov. 10, 2005

(51) Int. Cl.
*A61F 2/42* (2006.01)
(52) U.S. Cl. .................................................. 623/21.11
(58) Field of Classification Search ............... 623/16.11, 623/18.11, 21.11, 21.12, 21.15, 21.18, 21.19; 606/60, 61, 267; 433/169, 173–176
See application file for complete search history.

(56) References Cited

U.S. PATENT DOCUMENTS

| | | | |
|---|---|---|---|
| 3,579,831 A | 5/1971 | Stevens et al. | |
| 3,596,656 A * | 8/1971 | Kaute | 606/65 |
| 3,693,495 A | 9/1972 | Wagner | |
| 3,872,519 A | 3/1975 | Giannestras et al. | |
| 3,975,778 A | 8/1976 | Newton, III | |
| D274,359 S | 6/1984 | Christensen et al. | |
| 4,484,570 A | 11/1984 | Sutter et al. | |
| 4,552,532 A * | 11/1985 | Mozsary | 433/173 |
| 5,026,280 A * | 6/1991 | Durr et al. | 433/175 |
| 5,041,139 A | 8/1991 | Branemark | |
| 5,139,499 A * | 8/1992 | Small et al. | 606/73 |
| 5,234,300 A | 8/1993 | Flückiger | |
| 5,360,450 A | 11/1994 | Giannini | |
| 5,782,919 A | 7/1998 | Zdeblick et al. | |
| 5,814,071 A * | 9/1998 | McDevitt et al. | 606/232 |
| 5,827,285 A | 10/1998 | Bramlet | |
| 5,902,303 A * | 5/1999 | Eckhof et al. | 606/60 |
| 6,001,102 A * | 12/1999 | Barbera Alacreu | 606/73 |
| 6,117,173 A * | 9/2000 | Taddia et al. | 623/16.11 |
| 6,136,032 A | 10/2000 | Viladot Perice et al. | |
| 6,168,631 B1 | 1/2001 | Maxwell et al. | |
| 6,183,519 B1 | 2/2001 | Bonnin et al. | |
| 6,375,655 B1 | 4/2002 | Zdeblick et al. | |
| 6,471,707 B1 * | 10/2002 | Miller et al. | 606/73 |
| 6,488,712 B1 | 12/2002 | Tornier et al. | |
| 6,645,206 B1 | 11/2003 | Zdeblick et al. | |

(Continued)

OTHER PUBLICATIONS

Stephen Smith, MD, STA-PEG Subtalar Arthrorisis Implant, pp. 1-8 (Wright Medical Technology, Inc. , 2002) .

(Continued)

*Primary Examiner*—Anu Ramana
(74) *Attorney, Agent, or Firm*—Brooks Kushman P.C.

(57) ABSTRACT

An implant for insertion into a joint between articulating bones is provided. The implant includes a generally cylindrical metal body having a plurality of threads disposed thereon. The implant also includes a smooth polymeric portion that is configured to be disposed between the articulating bones of the joint. The polymeric portion provides a bearing surface for the articulating bones, and thus inhibits friction and irritation of the joint tissue. A pin is axially disposed through the polymeric portion and through the body and provides an attachment feature to facilitate rotation of the implant and engagement of the threads within the joint.

18 Claims, 4 Drawing Sheets

U.S. PATENT DOCUMENTS

| | | | |
|---|---|---|---|
| 6,666,868 B2 * | 12/2003 | Fallin | 606/73 |
| 7,033,398 B2 * | 4/2006 | Graham | 623/21.18 |
| 2003/0023315 A1 | 1/2003 | Tornier et al. | |
| 2003/0204265 A1 | 10/2003 | Short et al. | |

OTHER PUBLICATIONS

Stephen Smith, MD, STA-PEG Subtalar Arthrorisis Implant, 12 pages, (Wright Medical Technology, Inc., 2002).

* cited by examiner

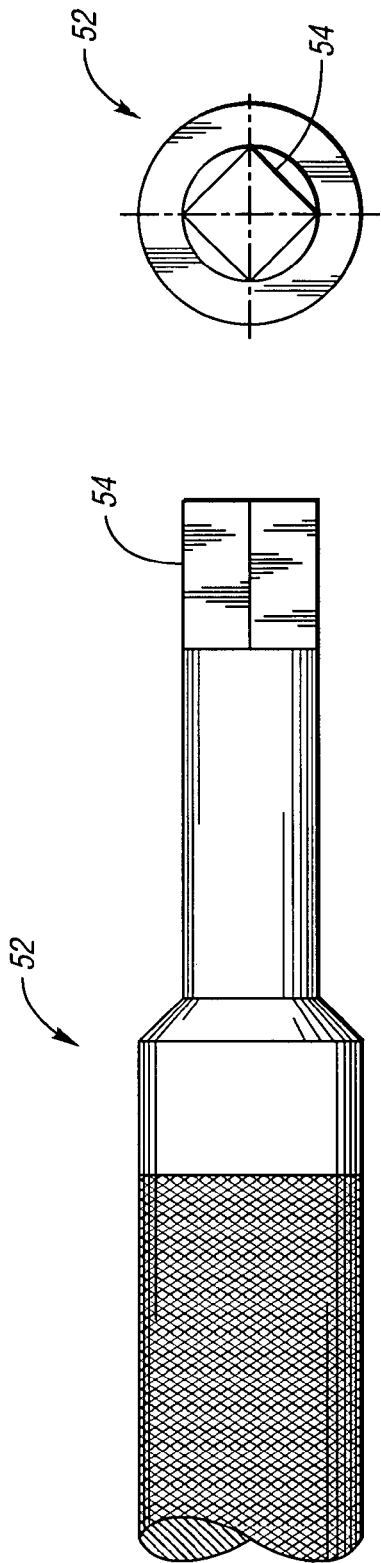
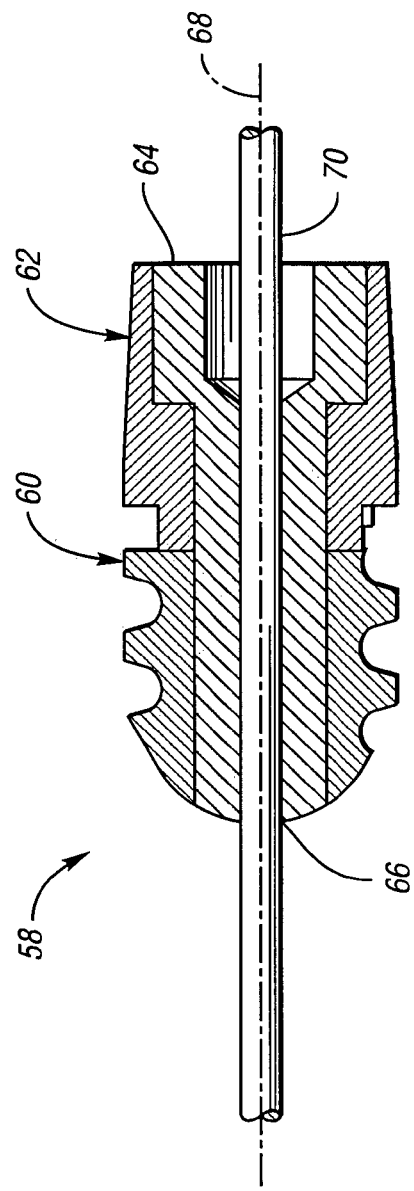

SUBTALAR IMPLANT

BACKGROUND OF THE INVENTION

1. Field of the Invention

The present invention relates to a subtalar implant, and in particular, an implant that can be used to correct a valgus deformity of the foot.

2. Background Art

For many years, surgeons have been attempting to correct valgus deformities of the foot—e.g., pes planus, or flatfoot—using a number of different techniques. One technique is to use a subtalar implant that is inserted into the tarsal sinus to reposition the calcaneus relative to the talus. One such device is described in U.S. Pat. No. 6,168,631 issued to Maxwell, et al. on Jan. 2, 2001. The implant described in Maxwell et al. is a metallic screw having external threads with slots formed in the threads. One limitation of the implant described in Maxwell, et al., is that there is no smooth surface on which the ankle bones can articulate. In fact, the talus and the calcaneus articulate on the same sharp-edged threads that are used to secure the implant within the joint. Such a configuration may lead to irritation of the articular bone and surrounding tissue.

One attempt to deal with this problem is described in U.S. Pat. No. 5,360,450 issued to Giannini on Nov. 1, 1994. Giannini describes an implant configured for insertion into the tarsal sinus for correction of pes planus. The Giannini implant is a two-piece device consisting of a cylindrical body and a screw which is configured for insertion into the cylindrical body. The cylindrical body includes a longitudinal incision which allows the body to expand when the screw is inserted into an axial hole. The entire implant is made from a bioresorbable material, such that removal of the implant is not necessary, rather, it is designed to be resorbed into the patient's body.

Although the Giannini implant does not require the ankle bones to articulate on metal threads, it nonetheless has a number of limitations. For example, the outer surface of the cylindrical body includes a plurality of grooves which are intended to provide a location for the growth of fibrous tissue. Necessarily, a plurality of rings abut the grooves such that the bones do not have a smooth surface on which to articulate. In addition, the implant described in Giannini relies on a wedge-effect using a bioresorbable material to secure the implant. Thus, the Giannini implant does not have the benefit of metal threads to securely hold the implant in the joint space.

One implant which uses a combination of metallic and polymeric components is described in U.S. Pat. No. 6,136,032 issued to Viladot Perice et al. on Oct. 24, 2000. The implant described in Viladot Perice et al. is a three-piece implant that is configured for insertion into the tarsal sinus. The Viladot Perice et al. implant includes a metal cone which is drawn up toward an implant head, thereby expanding an outer polyethylene cylinder. The polyethylene cylinder includes a plurality of fins which are shaped as barbs, tapering away from an outer surface of the cylinder and returning abruptly to the cylinder, thereby creating a sharp edge. The implant described in Viladot Perice et al. relies on a wedge-effect and the polyethylene fins to secure the implant. Thus, Viladot Perice et al. implant does not have the advantage of metal threads to secure the implant within the joint space. Moreover, the Viladot Perice et al. implant includes a plurality of sharp-edged fins which may irritate the joint tissue as the bones articulate.

Therefore, a need exists for an implant which can be used within the tarsal sinus that provides the advantage of threads to secure the implant in the joint space, and at the same time, provides a smooth surface on which the bones may articulate, thereby inhibiting friction and irritation within the joint.

SUMMARY OF THE INVENTION

Accordingly, the present invention provides an implant that can be used in the tarsal sinus and includes metal threads which secure the implant in the joint, and also includes a polymeric portion having a smooth surface on which the bones can articulate, thereby inhibiting friction and irritation of the joint tissue.

The invention also provides an implant for insertion into a joint between articulating bones. The implant includes a generally cylindrical metal body having a proximal end and a distal end, and defining a longitudinal axis. The body includes at least one thread disposed on an external surface thereof. The at least one thread is configured to engage tissue in the joint. A generally smooth polymeric portion is disposed adjacent the proximal end of the body. The polymeric portion includes an external surface configured to be disposed between articulating bones of the joint, thereby providing a bearing surface for the articulating bones.

The invention further provides an implant for insertion into a joint between articulating bones. The implant includes a generally cylindrical metal body having a proximal end and a distal end, and defining a longitudinal axis. The body includes at least one thread disposed on an external surface thereof. The at least one thread is configured to engage tissue in the joint, and to draw the implant into the joint when the body is rotated in one direction about the longitudinal axis. The body further includes a first axial hole disposed therethrough and generally parallel to the longitudinal axis. A polymeric portion is disposed adjacent the proximal end of the body. The polymeric portion includes an external surface configured to be disposed between articulating bones of the joint, thereby providing a bearing surface for the articulating bones. The polymeric portion further includes a second axial hole disposed therethrough and generally parallel to the longitudinal axis. An elongate member is disposed through the first and second axial holes. The elongate member has a proximal end and a distal end. The proximal end includes a first recess having at least one generally flat side to facilitate a rotation of the implant in one direction about the longitudinal axis for insertion into the joint.

The invention also provides a method of producing an implant for insertion into a joint between articulating bones. The implant includes a metal body and a polymeric portion. The metal body has at least one thread disposed on an external surface thereof, and the polymeric portion includes an external surface configured to be disposed between articulating bones in the joint, thereby providing a bearing surface for the articulating bones. The method includes disposing the polymeric portion adjacent a proximal end of the body such that a first axial hole in the body is generally aligned with a second axial hole in the polymeric portion. A pin is inserted through the first and second axial holes, and is secured to at least one of the polymeric portion and the body.

BRIEF DESCRIPTION OF THE DRAWINGS

FIGS. 11A and 11B show a surgical tool that can be used to insert the implant shown in FIG. 1; and FIG. 12 shows an alternative embodiment of the implant shown in FIG. 1, and a guide tool that can be used to help locate the implant within the joint.

DETAILED DESCRIPTION OF THE PREFERRED EMBODIMENT(S)

Figure 1:
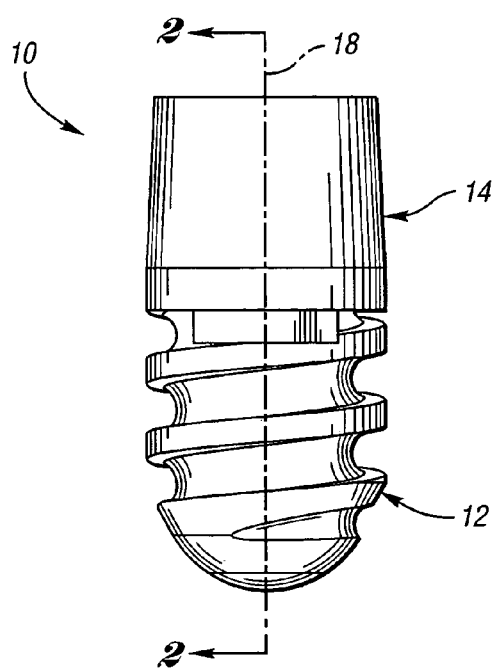
FIG. 1 is a side plan view of an implant in accordance with the present invention.
Figure 2:
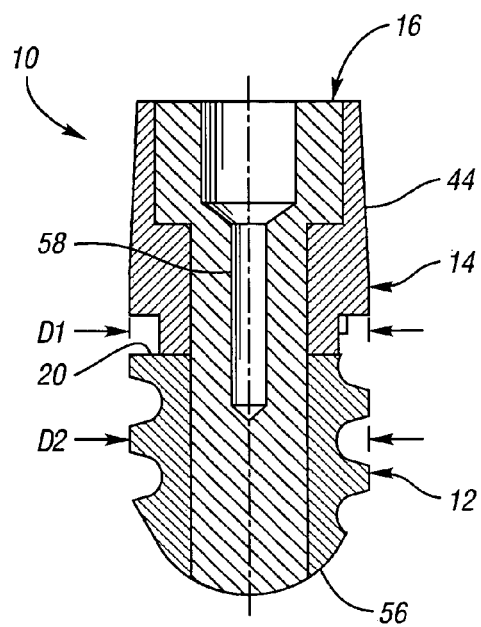
FIG. 2 is a sectional view of the implant shown in FIG. 1, taken through line 2-2.
Figure 3:
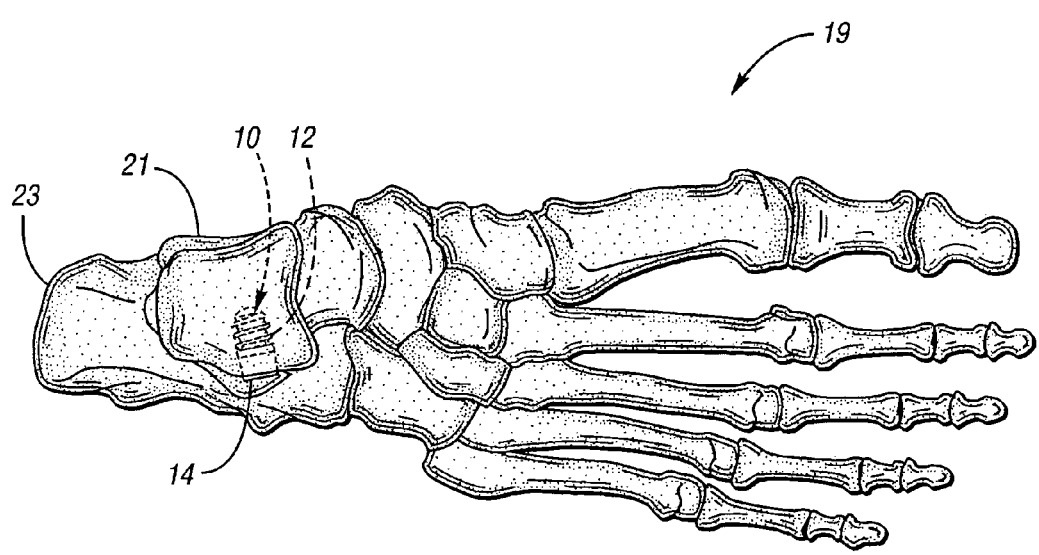
FIG. 3 is a side plan view of the bones of the foot illustrating the implant of FIG. 1 disposed in the tarsal sinus.
Figure 4:
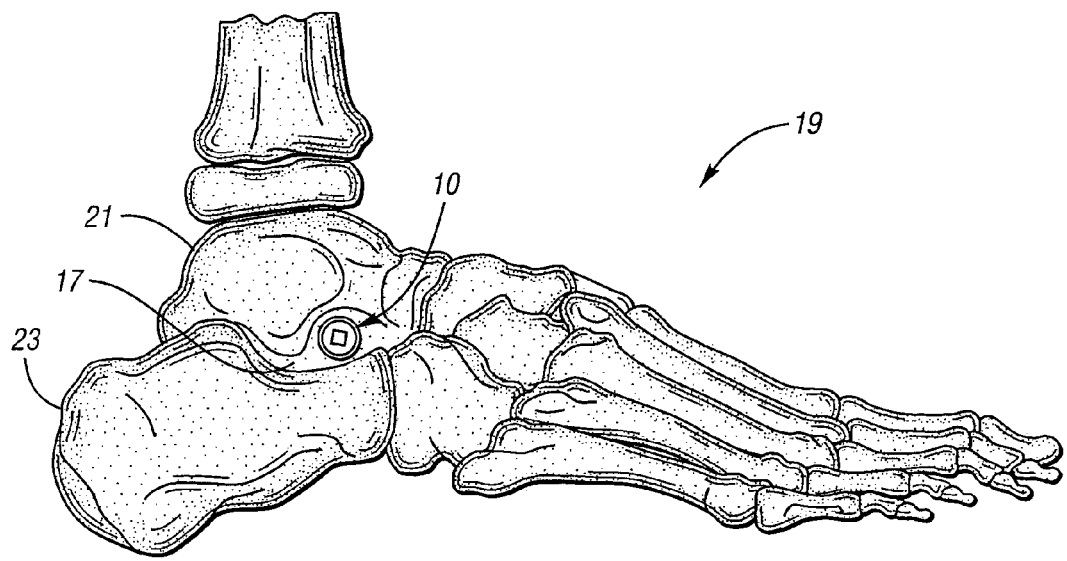
FIG. 4 is a top plan view of the foot bones and implant shown in FIG. 3.

FIG. 1 shows an implant 10 in accordance with the present invention. The implant 10 includes a metal body 12 and a polymeric portion 14. FIG. 2 shows a section of the implant 10 taken through line 2-2 in FIG. 1. As shown in FIG. 2, the implant 10 also includes an elongate member, or pin 16. The implant 10 is sized to fit in a joint in the human body, and in particular, a tarsal sinus 17 of a foot 19, as illustrated in FIG. 3. Of course, an implant, such as the implant 10, may be provided in different sizes to fit within different joints in the body. As shown in FIGS. 3 and 4, the implant 10 is inserted between a talus 21 and a calcaneus 23 of the foot 19. As described more fully below, the body 12 secures the implant 10 in the tarsal sinus 17, while the polymeric portion 14 provides a smooth bearing surface on which the talus 21 and the calcaneus 23 can articulate.

Figures 5, 6:
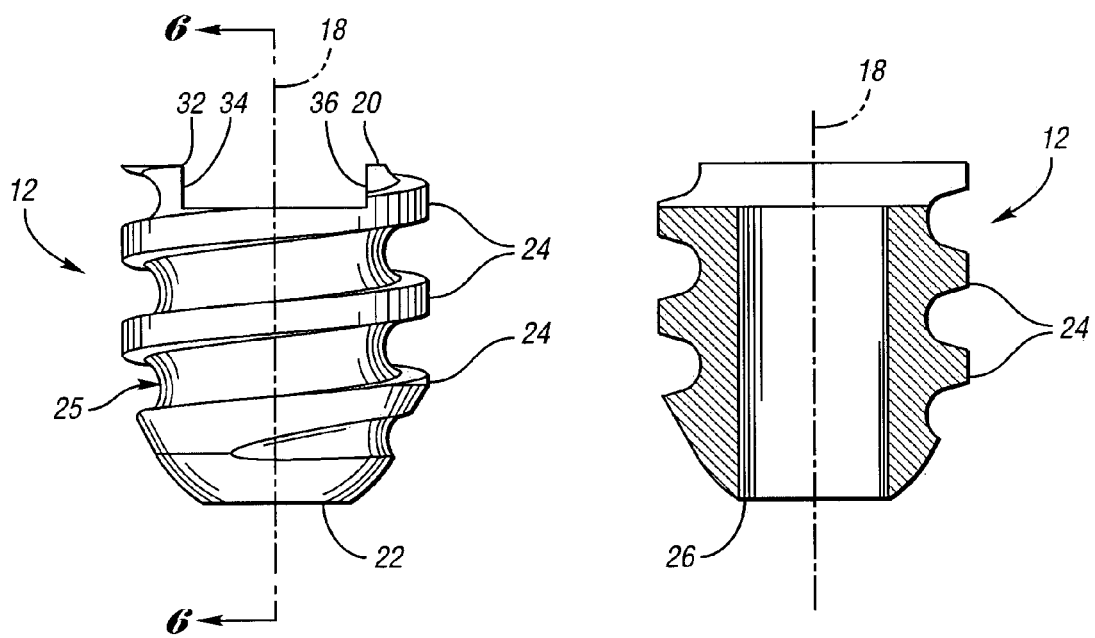
FIG. 5 is a side plan view of a body portion of the implant shown in FIG. 1.
FIG. 6 is a side sectional view of the body portion shown in FIG. 5, taken through line 6-6.

FIG. 5 shows a front plan view of the body 12. The body 12 has a generally cylindrical shape, and defines a longitudinal axis 18. The body 12 includes a proximal end 20 and a distal end 22, and also includes a plurality of threads 24 disposed on an external surface 25. It is worth noting that the present invention contemplates the use of smaller implants, which may include a single thread, rather than the plurality of threads 24 shown in FIG. 5. The threads 24 are configured to engage tissue in the tarsal sinus 17—see FIGS. 3 and 4—thereby securely fixating the implant 10 within the joint. As the implant 10 is rotated about the longitudinal axis 18, the body 12 is also rotated. As the body 12 is rotated, the threads 24 engage tissue within the joint and draw the implant 10 into the joint space.

FIG. 6 shows a sectional view of the body 12 taken through line 6-6 in FIG. 5. In this view, it is shown that the body 12 includes a first axial hole 26 that is generally parallel to the longitudinal axis 18. The first axial hole 26 is a through-hole that is configured to receive the pin 16. As explained more fully below, the pin 16 keeps the body 12 and the polymeric portion 14 secured to each other. The body 12 can be made from any metal that is effective to secure the implant 10 within a joint and is generally indicated for implantation into the human body. For example, titanium and titanium alloys, cobalt-chromium alloys, and stainless steel alloys may be used. In particular, a titanium alloy conforming to the American Society For Testing And Materials (ASTM) Standard F136 may be used.

Figure 7:
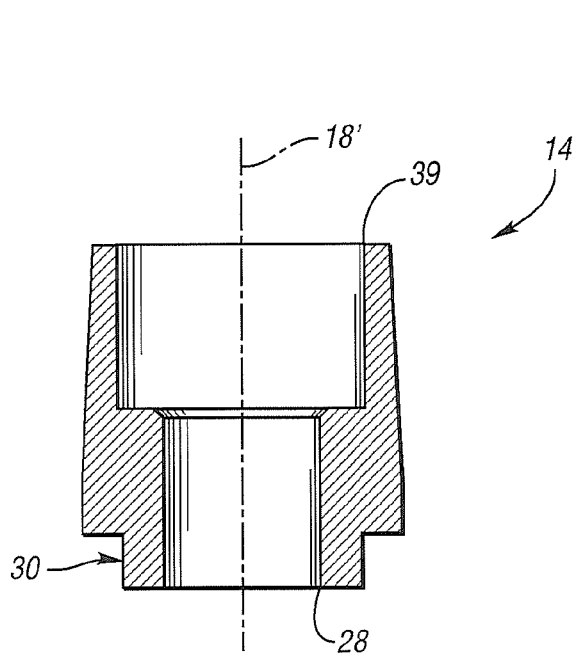
FIG. 7 is a side sectional view of a polymeric portion of the implant shown in FIG. 1.

FIG. 7 shows a side plan view of the polymeric portion 14. In this view, the polymeric portion 14 is shown as a section, which illustrates a second axial hole 28 which is generally parallel to the longitudinal axis 18' of the polymeric portion 14. The label 18' is used to designate the longitudinal axis of the polymeric portion 14, since it is not associated with the body 12; however, when the implant 10 is assembled, such as shown in FIG. 1, the axes 18, 18' will be generally coincident. This means that when the implant 10 is assembled, the first and second axial holes 26, 28 will be in general alignment, such that the pin 16 can be inserted through both the polymeric portion 14 and the body 12.

Figure 8:
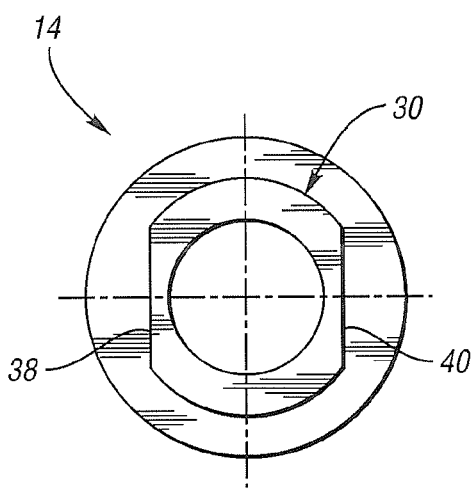
FIG. 8 is a bottom plan view of the polymeric portion shown in FIG. 7.

The polymeric portion 14 is configured to cooperate with a proximal end 20 of the body 12. In particular, the polymeric portion 14 includes a projection 30 which is configured to cooperate with a recess 32 in the body 12—see FIG. 5. As shown in FIG. 5, the recess 32 includes two flat sides 34, 36. The flat sides 34, 36 engage corresponding flat sides 38, 40 on the polymeric portion 14—see FIG. 8. The cooperation of the projection 30 and the recess 32 help to keep the polymeric portion 14 rotationally stable after the implant 10 is inserted into the joint. In particular, the implant 10 is rotated about the longitudinal axis 18 as it is inserted into the joint. Once it is within the joint, the threads 24 engage the joint tissue which inhibits further rotation of the body 12 even when the bones in the joint articulate. The cooperation of the projection 30 on the polymeric portion 14, and the recess 32 in the body 12, inhibits rotation of the polymeric portion 14 about the longitudinal axis 18. This provides additional stability to the implant 10, and helps to reduce wear inside the polymeric portion 14. This may increase the longevity of the implant 10, as well as reduce irritation of the joint tissue.

As shown in FIG. 7, the polymeric portion 14 includes a recess 39 which is configured to receive a portion of the pin 16. In particular, turning to FIG. 9, the pin 16 includes a shank 40 and a head 42. The recess 39 in the polymeric portion 14 is configured to receive the head 42 of the pin 16. The recess 39 is made deep enough so that the head 42 does not extend substantially beyond the polymeric portion 14 after the pin 16 is inserted through the first and second axial holes 26, 28—see FIG. 2. As shown in FIG. 2, the polymeric portion 14 is disposed adjacent the proximal end 20 of the body 12. The polymeric portion 14 includes a smooth external surface 44 that is configured to be disposed between articulating bones in a joint, such as the talus 21 and the calcaneus 23—see FIGS. 3 and 4. This provides a smooth bearing surface for the articulating bones.

The polymeric portion 14 can be made from any polymer that provides a good wear surface and is generally indicated for implantation into the human body. For example, ultra-high-molecular-weight polyethylene, conforming to ASTM Standard F648 may be used, though other polymeric materials are contemplated within the scope of the invention. As shown in FIG. 2, the polymeric portion 14 has a maximum diameter (D1) that is approximately equal to, but no greater than, the maximum diameter (D2) of the body 12. Moreover, the polymeric portion 14 is tapered along a length leading away from the body 12. Although such a configuration is not required, having the maximum diameter of the polymeric portion 14 less than or equal to the maximum diameter of the body 12 facilitates insertion of the implant 10 into the joint. In particular, it allows the implant 10 to be inserted without the polymeric portion 14 unnecessarily impinging upon joint tissue as the implant 10 is being inserted.

Figure 9:
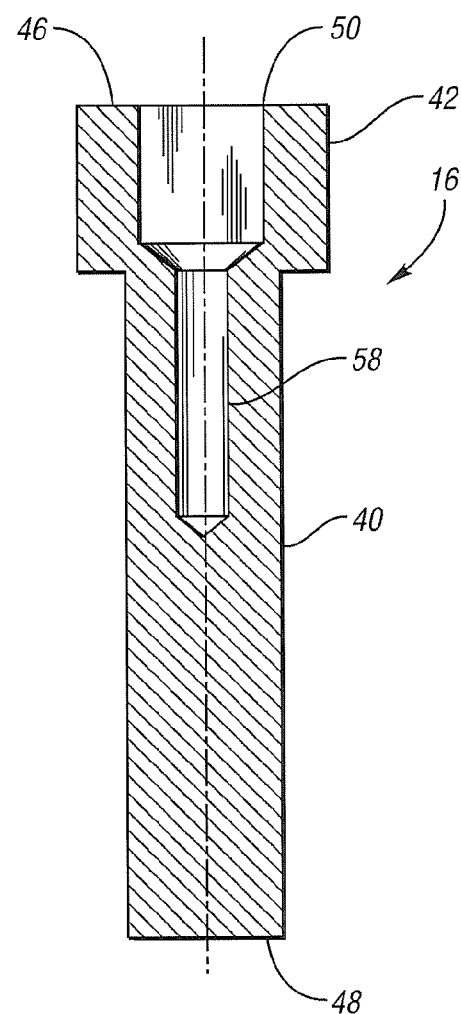
FIG. 9 is a side sectional view of a pin shown in FIG. 2.
Figure 10:
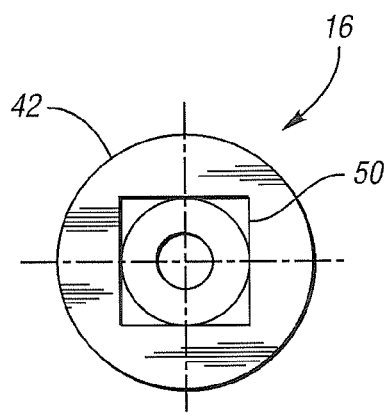
FIG. 10 is a top plan view of the pin shown in FIG. 9.

As shown in FIG. 9, the pin 16 includes a proximal end 46 and a distal end 48. The proximal end 46 of the pin 16 includes a recess 50 which has a generally square configuration—this is shown in FIG. 10, which is a top plan view of the pin 16. The square recess 50 is configured to receive a tool, such as the square-head driver 52 shown in FIGS. 11A and 11B. In fact, the recess 50 is an attachment feature which cooperates with the head 54 of the driver 52 to facilitate rotation of the implant 10 about the longitudinal axis 18, such that the implant 10 can be inserted into the joint. Although the embodiment of the pin 16 illustrated in the drawing figures includes a recess having four generally flat sides, other configurations are possible. For example, a generally circular recess having a single flat side would still facilitate rotation of an implant, such as the implant 10 about a longitudinal axis.

In order to produce an implant, such as the implant 10, the polymeric portion 14 is disposed adjacent the proximal end 20 of the body 12. The polymeric portion 14 and the body 12 can be attached to each other in any of a number of ways, and the use of the pin 16 provides one convenient and effective method. The pin 16 can be inserted through the first and second axial holes 26, 28, and specifically configured to be long enough to project beyond the proximal end 26 of the body 12. This facilitates welding the proximal end 48, or some portion of the pin 16 near the proximal end 48, to the proximal end 26 of the body 12. Welding the pin 16 to the body 12 provides the advantage of a strong attachment, and also seals the distal end 22 of the body 12 to prevent ingress of joint tissue and fluids.

Of course, welding the pin 16 to the body 12 requires that both components be made from materials that are compatible for welding. For example, if, as discussed above, the body 12 is made from a titanium alloy, it may be convenient to manufacture the pin 16 from the same alloy to ensure compatibility. After the pin 16 is welded to the body 12, the respective distal ends 48, 22 can be ground to a smooth radius, thereby creating an generally spherical end 56 as shown in FIG. 2. Although the embodiments illustrated in the drawing figures show a three-piece implant, the present invention contemplates the use of a two-piece implant having a metal body and polymeric portion attached to each other by any effective method, for example, a snap fit. The three-piece configuration illustrated in the drawing figures facilitates manufacturing and provides a fast and effective means of assembling an implant, such as the implant 10.

As shown in FIGS. 2 and 9, the pin 16 includes a blind hole 58 which may be included to facilitate manufacture of the recess 50. Alternatively, the hole can be disposed through the entire length of the pin, such as the pin 16. FIG. 12 shows an alternative embodiment of an implant 58 in accordance with the present invention. As with the implant 10, the implant 58 includes a body 60, a polymeric portion 62, and a pin 64. The pin 64 includes an aperture, or axial hole 66, which is disposed through the entire length of the pin 64. The axial hole 66 is generally parallel to a longitudinal axis 68 of the implant 58. The axial hole 66 is configured to receive a guide tool 70 which may be conveniently used by a surgeon to facilitate location and implantation of the implant 58 into the joint. The guide tool 70 may be a metal wire or other device which has the strength and flexibility to allow a surgeon to accurately guide the implant into the joint. Thus, the present invention provides an implant that is secured within the joint by metal threads, provides a smooth polymeric surface to inhibit friction and irritation of the joint, and is also easily located and inserted into the joint.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An implant for insertion into a joint between articulating bones, the implant comprising:
    a generally cylindrical metal body having a proximal end and a distal end, and defining a longitudinal axis, the body including at least one thread disposed on an external surface thereof, the at least one thread being configured to engage tissue in the joint, the body further including a first axial hole disposed therethrough;
    a generally smooth polymeric portion directly contacting the proximal end of the body and comprising a non-resorbable material, the polymeric portion including an external surface configured to directly contact articulating bones of the joint and to provide a bearing surface for the articulating bones, the polymeric portion further including a second axial hole disposed therethrough and generally aligned with the first axial hole, the polymeric portion having a maximum diameter that is no greater than a maximum diameter of the body, thereby facilitating insertion of the implant into the joint, the external surface of the polymeric portion and the external surface of the body defining an external surface of the implant; and
    an elongate member disposed through the first and second axial holes, thereby maintaining the polymeric portion and the body in close proximity to each other.

2. The implant of claim 1, wherein the polymeric portion is configured to cooperate with the proximal end of the body to inhibit rotation of the polymeric portion about the longitudinal axis when the body is fixed rotationally about the longitudinal axis.

3. The implant of claim 2, wherein the body includes a recess disposed in the proximal end and the polymeric portion includes a projection configured to cooperate with the recess to inhibit rotation of the polymeric portion about the longitudinal axis when the body is fixed rotationally about the longitudinal axis.

4. The implant of claim 1, wherein the polymeric portion has a decreasing taper along a length of the polymeric portion, in a direction away from the proximal end of the body thereby facilitating insertion of the implant into the joint and inhibiting contact between the polymeric portion and joint tissue when the implant is being inserted.

5. The implant of claim 1, wherein the elongate member has a proximal end and a distal end, and the distal end of the elongate member is welded to the distal end of the body, thereby securing the elongate member to the body.

6. The implant of claim 5, wherein the proximal end of the elongate member includes an attachment feature configured to cooperate with a tool to facilitate rotation of the implant in one direction about the longitudinal axis for insertion into the joint.

7. An implant for insertion into a joint between articulating bones, the implant comprising:
    a generally cylindrical metal body having a proximal end and a distal end, and defining a longitudinal axis, the body including at least one thread disposed on an external surface thereof, the at least one thread being configured to engage tissue in the joint, and to draw the implant into the joint when the body is rotated in one direction about the longitudinal axis, the body further including a first axial hole disposed therethrough and generally parallel to the longitudinal axis;
    a polymeric portion comprising a non-resorbable material directly contacting the proximal end of the body, the polymeric portion including an external surface configured to directly contact articulating bones of the joint and to provide a bearing surface for the articulating bones, the polymeric portion further including a second axial hole disposed therethrough and generally parallel to the longitudinal axis, the polymeric portion having a maximum diameter that is no greater than a maximum diameter of the body, thereby facilitating insertion of the implant into the joint, the external surface of the polymeric portion and the external surface of the body defining an external surface of the implant; and an elongate member disposed through the first and second axial holes, the elongate member having a proximal end and a distal end, the proximal end including a first recess having at least one generally flat side to facilitate rotation of the implant in one direction about the longitudinal axis for insertion into the joint.

8. The implant of claim 7, wherein the first recess includes four generally flat sides and is configured to receive a tool having a generally square driving portion.

9. The implant of claim 7, wherein the elongate member includes an aperture disposed therethrough, the aperture being generally parallel to the longitudinal axis and configured to receive a guide tool for facilitating insertion of the implant into the joint.

10. The implant of claim 7, wherein the polymeric portion is configured to cooperate with the proximal end of the body to inhibit rotation of the polymeric portion about the longitudinal axis when the body is fixed rotationally about the longitudinal axis.

11. The implant of claim 10, wherein the body includes a second recess disposed in the proximal end and the polymeric portion includes a projection configured to cooperate with the second recess to inhibit rotation of the polymeric portion about the longitudinal axis when the body is fixed rotationally about the longitudinal axis.

12. The implant of claim 7, wherein the polymeric portion has a decreasing taper along a length of the polymeric portion, in a direction away from the proximal end of the body thereby facilitating insertion of the implant into the joint and inhibiting contact between the polymeric portion and joint tissue when the implant is being inserted.

13. An implant for insertion into a joint between articulating bones, the implant comprising:

a generally cylindrical metal body having a proximal end and a distal end, and defining a longitudinal axis, the body including a first axial hole disposed therethrough, and at least one thread disposed on an external surface thereof, the at least one thread being configured to engage tissue in the joint;

a generally smooth polymeric portion directly contacting the proximal end of the body, the polymeric portion including a second axial hole disposed therethrough generally aligned with the first axial hole, and an external surface configured to directly contact articulating bones of the joint, thereby providing a bearing surface for the articulating bones, the polymeric portion having a maximum diameter that is no greater than a maximum diameter of the body, thereby facilitating insertion of the implant into the joint, the external surface of the polymeric portion and the external surface of the body defining an external surface of the implant; and an elongate member disposed through the first and second axial holes, and including an aperture disposed therethrough, the aperture being generally parallel to the longitudinal axis and configured to receive a guide tool for facilitating insertion of the implant into the joint.

14. The implant of claim 13, wherein the polymeric portion is configured to cooperate with the proximal end of the body to inhibit rotation of the polymeric portion about the longitudinal axis when the body is fixed rotationally about the longitudinal axis.

15. The implant of claim 14, wherein the body includes a recess disposed in the proximal end and the polymeric portion includes a projection configured to cooperate with the recess to inhibit rotation of the polymeric portion about the longitudinal axis when the body is fixed rotationally about the longitudinal axis.

16. The implant of claim 13, wherein the polymeric portion has a decreasing taper along a length of the polymeric portion, in a direction away from the proximal end of the body thereby facilitating insertion of the implant into the joint and inhibiting contact between the polymeric portion and joint tissue when the implant is being inserted.

17. The implant of claim 13, wherein the elongate member has a proximal end and a distal end, and the distal end of the elongate member is welded to the distal end of the body, thereby securing the elongate member to the body.

18. The implant of claim 17, wherein the proximal end of the elongate member includes an attachment feature configured to cooperate with a tool to facilitate rotation of the implant in one direction about the longitudinal axis for insertion into the joint.

* * * * *